Dec. 24, 1963 V. B. RODGERS Plant Pat. 2,330
ALMOND TREE
Filed Nov. 5, 1962
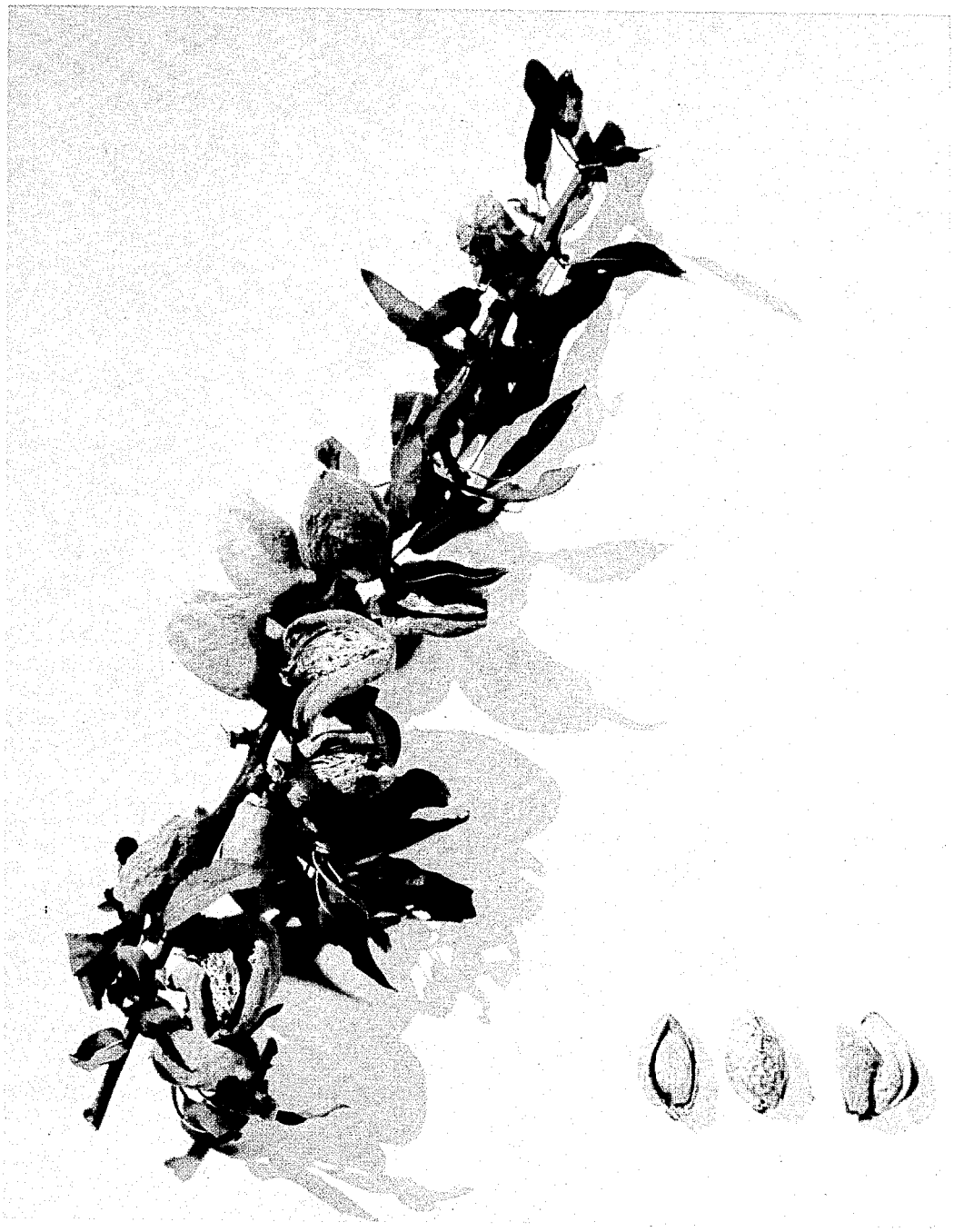
INVENTOR
Vincent B. Rodgers
Webster & Webster
ATTYS.

United States Patent Office

Plant Pat. 2,330
Patented Dec. 24, 1963

2,330
ALMOND TREE

Vincent B. Rodgers, P.O. Box 125, Ballico, Calif.

Filed Nov. 5, 1962, Ser. No. 235,590
1 Claim. (Cl. Plt.—30)

This discovery relates to a new and distinct variety of almond tree which originated as a bud sport or mutation on a mature Nonpareil almond tree growing in my cultivated orchard located near Ballico, California.

The discovery was made by me after I first observed the distinctive (small size) nuts on the belt of a hulling machine processing a crop from the above orchard, and subsequently—upon search—I located the mutation and selected it for propagation.

Asexual reproduction on my behalf was initially accomplished at a commercial nursery by budding onto S–37 rootstock, which was subsequently replanted and grown to maturity on my ranch located as aforesaid, and where the asexual reproductions were found to run true to the parent in all respects.

The present variety of almond tree is distinctively characterized, in comparison—for example—with the Nonpareil, and which has approximately the same harvest season, by a vigorously growing, rounded tree having smaller leaves well distributed about stronger branches and twigs; by blossoms smaller than the average, and which before unfolding are spherical in shape; and by the prolific bearing of small, paper shell nuts which produce a high percentage, by weight, of kernel to nut, and which kernels are of excellent quality and yet quite small, as is desirable for use in the manufacture of certain food products, such as candy.

An additional characteristic of the present variety of almond tree is that it is inter-fertile with the Mission, Jordanolo, Ne Plus, Ballico, and Merced, and possibly the Nonpareil, although tests with respect to the inter-fertility of the latter with the instant variety have not as yet been completed by me.

A further characteristic of the present variety of almond tree resides in the fact that there has been no appearance of the genetic failure known as "crazy top," or more properly bud failure; the latter being a very serious defect of the Jordanolo and Nonpareil varieties.

The drawing is an illustration, by photographic reproduction, of a twig with leaves and nuts as of the time of harvest; the drawing also showing, separately, one of the nuts with the hull thereon but opened, a nut as removed from the hull, and a nut with half of the shell broken away to expose the kernel.

Referring now more specifically to the botanical details of this new and distinct variety of almond tree, the following is an outline description thereof; all major color plate identifications being by reference to Maerz and Paul Dictionary of Color, except where common terms of color definition are employed:

Tree:
- *Density.*—Dense.
- *Size.*—Large.
- *Shape.*—Rounded.
- *Vigor.*—Vigorous.

Trunk:
- *Form.*—Stocky to medium.
- *Texture.*—Medium.

Branches:
- *Form.*—Stocky.
- *Strength.*—Stronger than Nonpareil.
- *Texture.*—Smooth.
- *Lenticels.*—Few.
- *Branching habits.*—Spreading.
- *Color.*—New wood—dull brown. Mature wood—dull brown.

Foliage: Quantity—abundant.

Leaves:
- *Size.*—Small. Average length—39.2 mm. Average width—14 mm.
- *Distribution.*—Well distributed about branches and twigs.
- *Shape.*—Lanceolate; abruptly pointed.
- *Thickness.*—Medium.
- *Texture.*—Smooth.
- *Margin.*—Crenate.
- *Petiole.*—Long; thick.
- *Glands.*—Average number—two. Position—opposite; base of leaf. Size—small. Form—globose.
- *Stipules.*—None.
- *Color.*—Growing season—medium green (23–L–8). At harvest—lighter yellow green (22–L–4).

Bloom:
- *Amount of bloom.*—Very heavy, but smaller than average.
- *Shape.*—Before unfolding, spherical.
- *Color.*—White.
- *Blooming period.*—With the Nonpareil and Merced. Medium as compared to other varieties.

Crop:
- *Bearing.*—Regular bearer.
- *Productivity.*—Very heavy.
- *Distribution of nuts on trees.*—In clusters on short spurs; well distributed.
- *Ripening period.*—Early, but subsequent to the Nonpareil.
- *Tenacity.*—Hangs well on tree; easy to harvest; easy to hull.

Hull:
- *Outer surface.*—Smooth.
- *Pits.*—Pitted.
- *Form.*—Regular.
- *Thickness.*—Thin.
- *Flesh.*—Tough.
- *Suture.*—Ridged.
- *Color.*—At harvest—yellow green (12–K–2) to grey (15–A–2).
- *Dihiscense.*—Opens freely.
- *Splitting.*—Along suture.

Nut:
- *Size.*—Small. Average length—26 mm. Average thickness—12.6 mm.
- *Form.* — Length/width — elongated. Width/thickness—plump.
- *Shell.*—Paper; soft; smooth. Outer shell—crumbling. Inner shell—soft; well sealed.
- *Color.*—Light brown or straw (9–D–4).
- *Pits.*—Small; irregular.
- *Base.*—Ventrally oblique.
- *Stem scar.*—Large; obtuse.
- *Apex.*—Acute.
- *Wing.*—Broad; thin; tapered toward base.
- *Inner surface.*—Light.
- *Ventral streak.*—Dark; broad.
- *Percent of kernel to nut on average samples.*—71.20 to 71.84.

Kernel:
- *Size.*—Small. Average length—20.3 mm. Average width—12 mm. Average thickness—8 mm.
- *Kernels per ounce on average sample.*—33.
- *Form.* — Length/width — elongated. Width/thickness—plump.
- *Base.*—Dorsally oblique.
- *Stem scar.*—Large; obtuse.
- *Apex.*—Obtuse; blunt.
- *Surface.*—Smooth.
- *Pellicle.*—Thin.
- *Pubescence.*—Smooth.

*Color.*—Light brown (12–K–8).
*Number of doubles.*—None.
*Flavor.*—Dry; sweet.
*Quality.*—Very good.

The prior varieties to which reference is made in this specification are unpatented, with the exception of the following:

S–37 (rootstock)—United States Plant No. 904
Ballico—United States Plant Patent No. 1,568.
Merced—United States Plant Patent No. 1,730.

The tree and its nuts herein described may vary in slight detail due to climatic and soil conditions under which this variety may be grown; the present description being of the variety as grown in the Central Valley of California.

The following is claimed:

A new and distinct variety of almond tree, as illustrated and described, characterized by a vigorously growing, rounded tree having small leaves well distributed about relatively strong branches and twigs; by blossoms smaller than the average and which before unfolding are spherical in shape; and by the prolific bearing of small, paper shell nuts having a high percentage, by weight, of kernel to nut, and which kernels are of small size and excellent quality.

No references cited.